United States Patent [19]
Waugh

[11] 4,021,864
[45] May 10, 1977

[54] ANKLE PROSTHESIS

[75] Inventor: Theodore Rogers Waugh, Santa Ana, Calif.

[73] Assignee: The Regents of the University of California, Berkeley, Calif.

[22] Filed: Apr. 14, 1976

[21] Appl. No.: 677,068

[52] U.S. Cl. .................................. 3/1.91; 128/92 C
[51] Int. Cl.² .......................................... A61F 1/24
[58] Field of Search ........................... 3/1.9–1.911, 3/1; 128/92 C

[56] References Cited
UNITED STATES PATENTS

| 3,839,742 | 10/1974 | Link | 3/1.91 |
|---|---|---|---|
| 3,872,519 | 3/1975 | Giannestras et al. | 3/1 |
| 3,889,300 | 6/1975 | Smith | 3/1.91 |
| 3,975,778 | 8/1976 | Newton | 3/1.91 |

Primary Examiner—Ronald L. Frinks
Attorney, Agent, or Firm—Connolly and Hutz

[57] ABSTRACT

A partial prosthesis for a human ankle joint has a metal tibial member with a flat triangular stem, which is implanted in the tibia. The base of the tibial member has a hollow toroidal section in its bottom. The talar member has an upper toroidal section which is engaged by that in the tibial member to provide articulation in the lateral/medial plane and in the anterior/posterior plane with inherent torsional stability.

12 Claims, 10 Drawing Figures

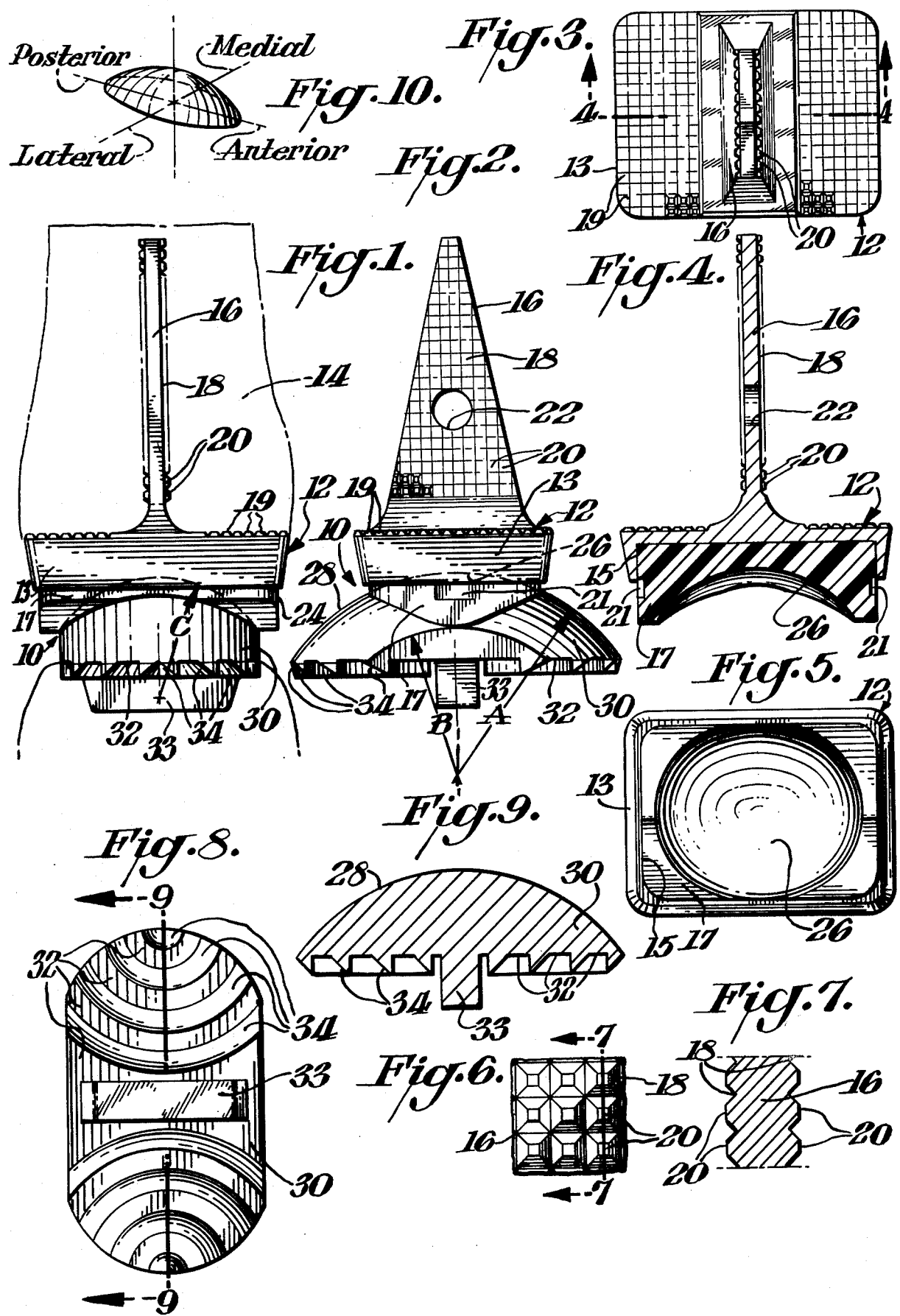

ANKLE PROSTHESIS

CROSS REFERENCE TO RELATED APPLICATIONS

None.

BACKGROUND OF THE INVENTION

Various ankle prostheses have been proposed including those described in U.S. Pat. Nos. 3,839,742 and 3,872,519. Such prosthetic joints provide a degree of articulation in extension and flexion and also some degree of rotational capability in the lateral/medial plane of the ankle. This causes a relatively high mechanical loading on the cemented connecting surfaces between the prosthetic members and the bones in which they are implanted. This results in inherent constraint between the mating prosthetic surfaces. An object of this invention is to provide a prosthetic ankle joint, which has more freedom of movement and a lower loading on the interfaces with the bones in which they are implanted.

SUMMARY

A partial prosthesis for a human ankle joint has a metal tibial member with a stem, which is implanted in the tibia and concave toroidal surface in its base. The metallic talar member has an upper toroidal surface upon which that in the tibial member rests to provide articulation in the lateral/medial plane and in the anterior/posterior plane with inherent torsional stability.

BRIEF DESCRIPTION OF THE DRAWING

Novel features and advantages of the present invention will become apparent to one skilled in the art from a reading of the following description in conjunction with the accompanying drawings wherein similar reference characters refer to similar parts and in which:

FIG. 1 is a front view in elevation of an ankle prosthesis with the bones in which it is implanted being shown in phantom outline;

FIG. 2 is a side view in elevation of the prosthesis shown in FIG. 1;

FIG. 3 is a top-plan view of the tibial member of the prosthesis shown in FIGS. 1 and 2;

FIG. 4 is a cross-sectional view taken through FIG. 3 along the line 4—4;

FIG. 5 is a bottom plan view of the tibial member shown in FIG. 4;

FIG. 6 is an enlarged view of a portion of the tibial stem shown in FIG. 2;

FIG. 7 is a cross-sectional view taken through FIG. 6 along the line 7—7;

FIG. 8 is a bottom plan view of the talar member shown in FIG. 1;

FIG. 9 is a cross-sectional view taken through FIG. 8 along the line 9—9; and

FIG. 10 is a schematic diagram showing the principal planes of movement of the prosthesis shown in FIGS. 1-9.

DESCRIPTION OF THE PREFERRED EMBODIMENTS

In FIG. 1 is shown an ankle prosthesis 10 having a tibial member 12 implanted in the tibia 14 by insertion of flat triangular stem 16 within the hollow center (not shown) of tibia 14. The tibial member 12 includes two parts, a stem base member 13 having a socket 15 that receives a biocompatible plastic base insert 17. Base member 13 is made of a biocompatible metal, such as Vitallium.

Vitallium is the trademark of Howmedica Inc. for a biocompatible metal. It is a special cobalt-chromium alloy developed and used for case partial and full dentures, and for internal applications by surgeons. Cobalt and chromium constitute over 90% of its composition. Sp.gr. 8.29; tensile strength, 100,000–120,000 lb/sq.in.; yeild point, 70,000–80,000 lb/sq.in.: Rockwell "C" hardness, 23–28; elongation, 15–20% modulus of elasticity in tension, 30,0000,000–32,000,000. When polished, it is exceedingly smooth and permanently lustrous. Its outstanding qualities are permanently inertness in relation to living tissues, and high degree of resistance to corrosion.

Stem 16 has a pair of toothed lateral surfaces 18 including spaced truncated pyramidal projections 20, shown enlarged in FIG. 6 and 7, to enhance retention in the bone in conjunction with a suitable bone cement. Retention is also assisted by circular hole 22 in stem 16.

Base member 13 has generally flat upper surface 24 disposed at right angles to stem 16.

Arranged on surface 24 are truncated pyramidal teeth 19 that help secure the tibial member.

Concave surface 26 in the bottom of base insert 17 engages the convex upper surface 28 of talar member 30. Insert 17 is, for example, made of a biocompatible plastic material such as ultrahigh molecular weight polyethylene. Base insert 17 is held in socket 15 via an interference or close fit, so that the replacement of the insert can be quickly performed without removal of tibial member 12 from the tibia bone.

Indents 21 are provided in end walls 23 to allow for insertion of the tips of a gripping tool (not shown) to facilitate removal of insert 17 from base 13 of tibial member 12.

The bottom of talar member 30 has as centrally positioned stem 33 that is disposed to right angles to bottom surface 32. In addition, the bottom 32 of talar member 30 is toothed by a series of opposed arcuate teeth 34 in FIGS. 8 and 9 which together with stem 33 are cemented into the talus by a suitable bone cement.

The subject prosthesis incorporates an articulation surface in the form of a toroidal sector — which is defined by different radii in the two principal planes of motion. The toroidal surface provides for articulation in the lateral/medial plane (also shown in FIG. 1) and in the anterior/posterior plane (also shown in FIG. 2) and has inherent torsional stability (along tibial axis). This is extremely important for an ankle prosthesis. The majority of prosthesis designs currently available only provide for one degree of freedom duplicating anatomical motion. However, when disturbing forces in the lateral/medial plane are imposed on the implant, the constraining reactions applied at the talar bone/-prosthesis interface may be sufficient to cause failure of the cement fixation.

The toroidal sections of prosthesis 10 have, for example, the following radii of curvature. In FIG. 2, the major radius A of concave toroidal section 26 and convex toroidal section 28 in the anterior/posterior plane is for example about one inch or 25.4 mm. Minor radius B of talar member 30 is, for example, three-quarters of an inch or 19.00 mm. Radius C in the lateral/medial plane of both of the toroidal surfaces shown in FIG. 1 is, for example, 0.594 inch of 15.08 mm.

I claim:

1. A partial prosthesis for a human ankle joint having a tibia and a talus comprising a tibial member, said tibial member having a tibial base, a tibial stem substantially centrally disposed upon the tibial base and extending upwardly therefrom to provide means for connecting said tibial member of the tibia, a concave toroidal section in the bottom of said tibial base, a talar member, a talar stem substantially centrally disposed upon the talar base extending downwardly for attaching it to said talus, a substantially convex toroidal section upon the upper surface of said talar member, said prosthesis having lateral/medial and anterior/posterior planes of movement, said toroidal sections each having a longer radius of curvature in said anterior/posterior plane than the radius of curvature in said lateral/medial plane whereby articulation is provided between the members in both planes with inherent stability.

2. A prosthesis as set forth in claim 1 wherein the major portion of the tibial base is comprised of biocompatible metal and an insert including the concave toroidal section is comprised of ultrahigh molecular weight polyethylene.

3. A prosthesis as set forth in claim 2 wherein said tibial stem is substantially flat with a triangular shape in said anterior/posterior plane.

4. A prosthesis as set forth in claim 3 wherein the sides of said tibial stem are toothed by truncated pyramidal projections.

5. A prosthesis as set forth in claim 4 wherein said tibial stem also includes a hole for assisting retention.

6. A prosthesis as set forth in claim 1 wherein said tibial base is substantially rectangular.

7. A prosthesis as set forth in claim 6 wherein central portions of the bottom of the tibial base in said anterior/posterior plane are disposed lower than the outer portions whereby they engage over the toroidal section on the talar member.

8. A prosthesis as set forth in claim 1 wherein retaining surface means are provided on said talar base and the retaining surface means is comprised of arcuate teeth.

9. A prosthesis as set forth in claim 8 wherein said arcuate teeth are disposed convexly away from each other on both sides of said centrally-positioned stem projecting from the bottom of said talar member.

10. A prosthesis as set forth in claim 1 wherein said talar member is comprised of biocompatible metal.

11. A prosthesis as set forth in claim 1 wherein the tibial base has a substantially flat upper surface.

12. A prosthesis as set forth in claim 11 wherein the tibial base surface is toothed by truncated pyramidal projections.

* * * * *